United States Patent
Coulomb

(10) Patent No.: US 9,382,501 B2
(45) Date of Patent: Jul. 5, 2016

(54) PYRAN AS FLORAL ODORANT

(71) Applicant: FIRMENICH SA, Geneva (CH)

(72) Inventor: Julien Coulomb, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/767,560

(22) PCT Filed: Feb. 4, 2014

(86) PCT No.: PCT/EP2014/052114
§ 371 (c)(1),
(2) Date: Aug. 12, 2015

(87) PCT Pub. No.: WO2014/124834
PCT Pub. Date: Aug. 21, 2014

(65) Prior Publication Data
US 2015/0368586 A1    Dec. 24, 2015

(30) Foreign Application Priority Data
Feb. 12, 2013 (EP) .................................. 13154879

(51) Int. Cl.
| | |
|---|---|
| *C11B 9/00* | (2006.01) |
| *A61Q 5/06* | (2006.01) |
| *A61Q 15/00* | (2006.01) |
| *C11D 3/20* | (2006.01) |
| *C11D 3/50* | (2006.01) |
| *A61K 8/49* | (2006.01) |
| *C07D 309/26* | (2006.01) |
| *C07D 309/06* | (2006.01) |

(52) U.S. Cl.
CPC ............... *C11B 9/008* (2013.01); *A61K 8/498* (2013.01); *A61Q 5/06* (2013.01); *A61Q 15/00* (2013.01); *C07D 309/06* (2013.01); *C07D 309/26* (2013.01); *C11D 3/2096* (2013.01); *C11D 3/50* (2013.01)

(58) Field of Classification Search
CPC .......... C11B 9/008; A61Q 5/06; A61Q 15/00; C11D 3/2096; C11D 3/50; A61K 8/498; C07D 309/26; C07D 309/06
See application file for complete search history.

(56) References Cited

U.S. PATENT DOCUMENTS

| | | | |
|---|---|---|---|
| 2,947,780 | A | 8/1960 | Teegarden et al. |
| 4,007,137 | A | 2/1977 | Sanders et al. |

OTHER PUBLICATIONS

International Search Report and Written Opinion, application PCT/EP2014/052114, mailed Mar. 4, 2014.
Kula J. et al., Perfumer & Flavorist, vol. 17, n° 5, 1992, 77-92.

*Primary Examiner* — Samantha Shterengarts
*Assistant Examiner* — Matt Mauro
(74) *Attorney, Agent, or Firm* — Winston & Strawn LLP

(57) ABSTRACT

The present invention relates to a composition of matter comprising 1) at least 70% of at least a compound of formula (I) in the form of any one of its stereoisomers or a mixture thereof, and wherein R represents —a hydrogen atom and the dotted line represents a carbon-carbon single or double bond; or —a CH$_2$ group bonded with C4 and C5 and the dotted line represents a carbon-carbon single bond; 2) at most 30% of at least a compound of formula (II) in the form of any one of its stereoisomers or a mixture thereof, and wherein R represents —a hydrogen atom and the dotted line represents a carbon-carbon single or double bond; or —a CH$_2$ group bonded with C4 and C5 and the dotted line represents a carbon-carbon single bond; and wherein the percentages are w/w percentages relative to the total weight of the composition. Said compositions are useful perfuming ingredients of the floral, lily of the valley type.

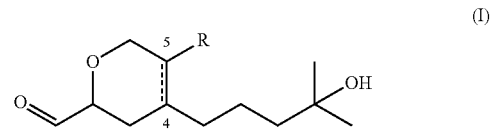

(I)

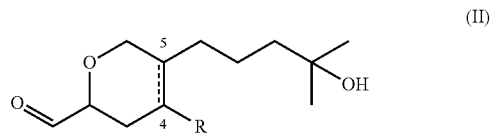

(II)

21 Claims, No Drawings

PYRAN AS FLORAL ODORANT

TECHNICAL FIELD

The present invention relates to the field of perfumery. More particularly, it concerns the use as perfuming ingredient of a composition of matter comprising derivatives of formula (I) and/or (II) as defined below, which are useful perfuming ingredients of the floral, lily of the valley type. Therefore, following what is mentioned herein, the present invention comprises the invention's compound as part of a perfuming composition or of a perfuming consumer product.

PRIOR ART

To the best of our knowledge, the invention's compounds of formula (I) are novel.

To the best of our knowledge, the closest analogue known in the perfumery is the chemical known as Lyral® (4-(4-hydroxy-4-methylpentyl)-3-cyclohexene-1-carboxaldehyde plus as minor product, the isomer 3-(4-hydroxy-4-methyl-pentyl)-3-cyclohexene-1-carboxaldehyde; origin: International Flavors & Fragrances, Inc., New York, USA) described in U.S. Pat. No. 2,947,780. Moreover U.S. Pat. No. 4,007,137 clearly indicates that the isomer 3-(4-hydroxy-4-methylpentyl)-3-cyclohexene-1-carboxaldehyde is an undesired component (see U.S. Pat. No. 4,007,137 column 5, line 45).

These prior art documents do not report or suggest any organoleptic properties of the compounds of formula (I) or (II) and do not report or suggest any use of said compounds in the field of perfumery.

DESCRIPTION OF THE INVENTION

We have now surprisingly discovered that a composition of matter comprising:
1) at least 70% of at least a compound of formula

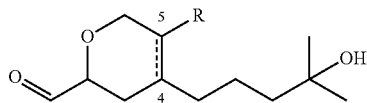

(I)

in the form of any one of its stereoisomers or a mixture thereof, and wherein R represents
a hydrogen atom and the dotted line represents a carbon-carbon single or double bond; or
a CH$_2$ group bonded with C4 and C5 and the dotted line represents a carbon-carbon single bond;
2) at most 30% of at least a compound of formula

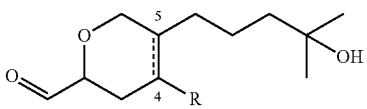

(II)

in the form of any one of its stereoisomers or a mixture thereof, and wherein R represents
a hydrogen atom and the dotted line represents a carbon-carbon single or double bond; or
a CH$_2$ group bonded with C4 and C5 and the dotted line represents a carbon-carbon single bond; and
wherein the percentages are w/w percentages relative to the total weight of the composition;
can be used as perfuming ingredient, for instance to impart odor notes of the floral, lily of the valley type.

For the sake of clarity, by the expression "any one of its stereoisomers", or the similar, it is meant the normal meaning understood by a person skilled in the art, i.e. that the compound can be a pure enantiomer (if chiral) or diastereomer (if the dotted line represents a single bond).

For the sake of clarity, by the expression "wherein the dotted line represents a carbon-carbon single/double bond", or the similar, it is meant the normal meaning understood by a person skilled in the art, i.e. that the whole bonding (solid and dotted line) between the carbon atoms connected by said dotted line, e.g. carbon 4 and 5, is a carbon-carbon single or double bond.

According to a particular embodiment of the invention, said dotted line and R have simultaneously the same meaning in formulae (I) and (II).

According to any one of the above embodiments of the invention, R represents a hydrogen atom and the dotted line represents a carbon-carbon single or double bond.

According to any one of the above embodiments of the invention, R represents a hydrogen atom and the dotted line represents a carbon-carbon double bond.

According to any one of the above embodiments of the invention, in said composition of matter the compounds of formula (I) represent at least 75%, and the compounds of formula (II) at most 25%, of the total weight of the composition.

According to any one of the above embodiments of the invention, in said composition of matter the compounds of formula (I) represent at least 85%, and the compounds of formula (II) at most 15%, of the total weight of the composition.

According to any one of the above embodiments of the invention, in said composition of matter, the compounds of formula (I) represent at least 95% of the total weight of the composition.

As specific examples of the invention's compounds, one may cite, as non-limiting example, a composition comprising 88% of 4-(4-hydroxy-4-methylpentyl)-3,6-dihydro-2H-pyran-2-carbaldehyde and 12% of 5-(4-hydroxy-4-methylpentyl)-3,6-dihydro-2H-pyran-2-carbaldehyde (also mentioned as Composition 1 in the examples) which possesses a smooth, soft and balanced lily of the valley odor of an outstanding tenacity and exalt the white flower aspect of the composition to which it is added. The organoleptic profile of this compound is very similar to the one of the well known perfumery ingredient Lyral® (mentioned above in the prior art section), in particular in what concerns the odor, as well as the tenacity and the radiance.

Such similitude of odor properties is particularly surprising, since the replacement of a CH$_2$ group by an oxygen atom is known to dramatically change the physic-chemical properties of a compound (such as log P or vapor pressure) and therefore its interaction with the olfactive receptors. For instance, the calculated values of the invention's compound compared to that of the prior art are for log P 1.57 vs 3.32, and for Vp 2.31 mPa vs 3.64 mPa, respectively.

For the sake of clarity the "log P" is the logarithm of the partition coefficient between water and octanol, and the vapor pressure has the standard meaning in the art. Said log P and vapor pressure are calculated values and can be obtained according to the program EPI suite (4.0); EPA (US Environmental Protection Agency) and Syracuse Research Corporation (SRC), 2000.

Furthermore, such similitude of odor properties is also surprising since the prior art composition comprises as main, and only desirable isomer, the compound wherein the carbaldehyde group and the chain group are para, while the present composition comprises as main, and most preferred isomer, the compound wherein the carbaldehyde group and the chain group are meta.

As other example, one may cite a composition comprising 88% of 4-(4-hydroxy-4-methylpentyl)tetrahydro-2H-pyran-2-carbaldehyde and 12% of 5-(4-hydroxy-4-methylpentyl)tetrahydro-2H-pyran-2-carbaldehyde, which possesses an odor similar to the one mentioned above but distinguishes itself by having also a lactonic, mandarin note.

According to a particular embodiment of the invention, the invention's composition is a composition comprising 88% of 4-(4-hydroxy-4-methylpentyl)-3,6-dihydro-2H-pyran-2-carbaldehyde and 12% of 5-(4-hydroxy-4-methylpentyl)-3,6-dihydro-2H-pyran-2-carbaldehyde.

As mentioned above, the invention concerns the use of the invention's composition of matter as perfuming ingredient. In other words, it concerns a method to confer, enhance, improve or modify the odor properties of a perfuming composition or of a perfumed article, which method comprises adding to said composition or article an effective amount of the invention's composition of matter. By "use of the invention's composition of matter" it has to be understood here also the use of any composition containing the invention's composition of matter and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, the invention's composition of matter as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- und Geliermittel in Lebensmitteln, Band 2 der Schriftenreihe Lebensmittelchemie, Lebensmittelqualitat, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I) or formula (II). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are to well known to a person skilled in the art.

An invention's composition consisting of at least the invention's composition of matter and at least one perfumery carrier represents a particular embodiment of the invention as well as a perfuming composition comprising at least the invention's composition of matter, at least one perfumery carrier, at least one perfumery base, and optionally at least one perfumery adjuvant.

For the sake of clarity, it is also understood that any mixture resulting directly from a chemical synthesis, e.g. a reaction medium without an adequate purification, in which the invention's composition of matter would be involved as a starting, intermediate or end-product could not be considered as a perfuming composition according to the invention as far as said mixture does not provide the inventive composition of matter in a suitable form for perfumery. Thus, unpurified reaction mixtures are generally excluded from the present invention unless otherwise specified.

Furthermore, the invention's composition of matter can also be advantageously used in all the fields of modern perfumery, i.e. fine or functional perfumery, to positively impart or modify the odor of a consumer product into which said invention's composition of matter is added. Consequently, another object of the present invention is represented by a perfuming consumer product comprising, as perfuming ingredient, the invention's composition of matter, as defined above.

The invention's composition of matter can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of the invention's composition of matter. For the sake of clarity, said perfuming consumer product is a non-edible product.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's composition of matter, so that it may be necessary to protect the latter from premature decomposition, for example by encapsulation or by chemically bounding it to another chemical which is suitable to release the invention's composition of matter upon a suitable external stimulus, such as an enzyme, light, heat or a change of pH.

The proportions in which the composition of matter according to the invention can be incorporated into the various aforementioned articles or compositions vary within a wide range of values. These values are dependent on the nature of the article to be perfumed and on the desired organoleptic effect as well as the nature of the co-ingredients in a given base when the composition of matter according to the invention are mixed with perfuming co-ingredients, solvents or additives commonly used in the art.

For example, in the case of perfuming compositions, typical concentrations are in the order of 0.5% to 25% by weight, or even more, of the invention's composition of matter based on the weight of the composition into which they are incorporated. Concentrations lower than these, such as in the order of 0.1% to 10% by weight, can be used when said the invention's composition of matter is incorporated into perfumed articles, percentage being relative to the weight of the article.

The invention's composition of matter can be prepared according to a method comprising a Diels Alder reaction between an alkyl glyoxylate and myrcenol to obtain the esters, or a mixture of esters, of formula

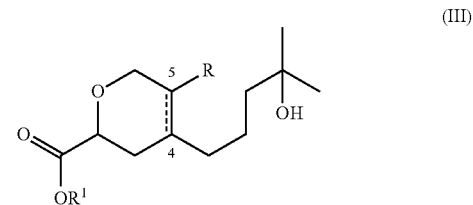

(III)

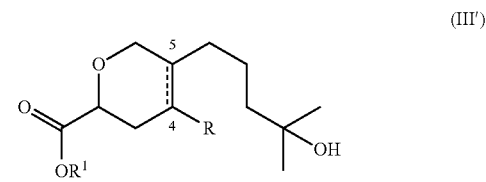

(III')

wherein the dotted line and R have the same meaning as for formula (I) and $R^1$ is a $C_{1-4}$ alkyl group.

Said ester (III) can be reduced to the desired product or composition of matter according standard methods well known to a person skilled in the art.

The compounds of formula (I), (II), (III) and (III') are novel compounds. Therefore another object of the present invention is a compound of formula

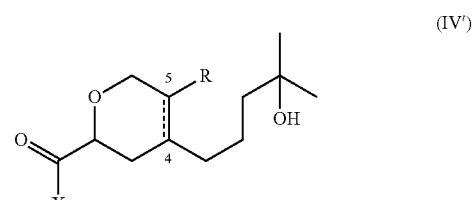

(IV')

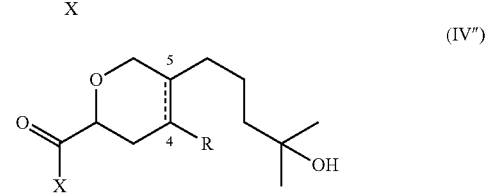

(IV")

wherein X represent a hydrogen atom or a $OR^1$ group, $R^1$ being a $C_{1-4}$ alkyl group; and R represents a hydrogen atom and the dotted line represents a carbon-carbon single or double bond; or a $CH_2$ group bonded with C4 and C5 and the dotted line represents a carbon-carbon single bond; and said compound (IV') or (IV") being in the form of any one of its stereoisomers or a mixture thereof.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

A composition of matter comprising 88% of 4-(4-hydroxy-4-methylpentyl)-3,6-dihydro-2H-pyran-2-carbaldehyde and 12% of 5-(4-hydroxy-4-methylpentyl)-3,6-dihydro-2H-pyran-2-carbaldehyde (also referred to as Composition 1)

a) ethyl 4-(4-hydroxy-4-methylpentyl)-3,6-dihydro-2H-pyran-2-carboxylate (as main compound) and 5-(4-hydroxy-4-methylpentyl)-3,6-dihydro-2H-pyran-2-carboxylate (as minor compound)

A mixture of ethyl glyoxylate (50% solution in toluene) (38.6 mL, 194 mmol) and myrcenol (20 g, 130 mmol) was heated to reflux for 29 h. Excess ethyl glyoxylate and toluene were evaporated, and the residue was purified by flash column chromatography on silica gel using gradient mixtures of heptane and ethyl acetate (85:15 to 60:40) to afford pure ester (80% yield) as a colorless oil and a 88:12 mixture of regioisomers.

Major isomer:
$^1$H NMR: 5.44 (m, 1H), 4.36 (m, 1H), 4.18-4.28 (m, 4H), 2.21-2.37 (m, 2H), 2.01-2.05 (m, 2H), 1.42-1.53 (m, 4H), 1.31 (t, J=7.1 Hz, 3H), 1.22 (s, 6H)
$^{13}$C NMR: 171.6 (s), 134.4 (s), 119.3 (d), 72.4 (d), 70.8 (s), 65.5 (t), 61.1 (t), 43.3 (t), 37.2 (t), 30.7 (t), 29.3 (q, 2C), 21.8 (t), 14.2 (q).

b) 4-(4-hydroxy-4-methylpentyl)-3,6-dihydro-2H-pyran-2-carbaldehyde (as main compound) and 5-(4-hydroxy-4-methylpentyl)-3,6-dihydro-2H-pyran-2-carbaldehyde (as minor compound)

To a solution of ethyl 4-(4-hydroxy-4-methylpentyl)-3,6-dihydro-2H-pyran-2-carboxylate (5.00 g, 19.5 mmol) in dichloromethane at −78° C. was added DIBAL (1 M in dichloromethane, 48.8 mL, 48.8 mmol) over a 45 minutes period and the reaction was stirred at −78° C. for an additional hour. It was quenched with 50 mL of methanol, followed by 100 mL of water and 100 mL of a 5% HCl aqueous solution. The aqueous layer was extracted three times with diethyl ether, the combined organic extracts were dried over sodium sulfate and the solvent was evaporated. The residue was purified by bulb-to-bulb distillation (155-160° C., 10$^{-3}$ mbar) to afford desired product (51% yield) as a colorless oil and in the form of a 88:12 mixture of regioisomers.

4-(4-hydroxy-4-methylpentyl)-3,6-dihydro-2H-pyran-2-carbaldehyde $^1$H NMR: 9.74 (s, 1H), 5.46 (m, 1H), 4.19-4.37 (m, 2H), 4.05 (dd, J=9.0, 4.9 Hz, 1H), 2.02-2.25 (m, 4H), 1.42-1.55 (m, 4H), 1.22 (s, 6H)
$^{13}$C NMR: 201.8 (d), 134.1 (s), 119.6 (d), 77.7 (d), 70.9 (s), 65.4 (t), 43.3 (t), 37.2 (t), 29.3 (q, 2C), 28.0 (t), 21.8 (t).

A composition of matter comprising 88% of 4-(4-hydroxy-4-methylpentyl)tetrahydro-2H-pyran-2-carbaldehyde and 12% of 5-(4-hydroxy-4-methylpentyl)tetrahydro-2H-pyran-2-carbaldehyde In a 70-mL autoclave were placed 4-(4-hydroxy-4-methylpentyl)-3,6-dihydro-2H-pyran-2-carbaldehyde (1.75 g, 8.24 mmol) and 5% Pd/C (114 mg) in 20 mL ethyl acetate. The autoclave was sealed, purged with argon and reacted at room temperature. under 45 bar pressure of H$_2$. After one hour, the autoclave was purged with argon, opened, the catalyst was filtered and the solvent was evaporated. The residue was purified by flash column chromatography on silica gel (Heptane/AcOEt 4:6) and bulb-to-bulb distillation (10$^{-3}$ mbar, 130° C.) to afford desired product (95% yield) as a colorless oil and in the form of a 73:15:12 mixture of isomers.

Major isomer:
$^1$H NMR: 9.61 (s, 1H), 4.13 (m, 1H), 3.79 (dd, J=12.0, 2.5 Hz, 1H), 3.49 (dt, J=12.0, 2.1 Hz, 1H), 1.93 (m, 1H), 1.25-1.67 (m, 10H), 1.22 (s, 6H).
$^{13}$C NMR: 201.5 (d), 81.6 (d), 70.9 (s), 68.0 (t), 43.9 (t), 37.3 (t), 34.8 (d), 32.8 (t), 32.3 (t), 29.3 (q, 2C), 21.0 (t).

Example 2

Preparation of a Perfuming Composition

An Eau de Cologne for man, of the woody-citrus type, was prepared by admixing the following ingredients:

| Parts by weight | Ingredient |
|---|---|
| 10 | 1,1-Dimethyl-2-phenylethyl acetate |
| 10 | Geranyl acetate |
| 200 | Bergamot essential oil |
| 10 | 10%* 4-(4-Hydroxy-1-phenyl)-2-butanone |
| 30 | Citral |
| 500 | Lemon essential oil |
| 90 | 10%* Galbanum essential oil |
| 90 | Clove essential oil |
| 100 | Habanolide ®[1] |
| 200 | Lavender essential oil |
| 70 | Linalol |
| 120 | Marjoram essential oil |
| 50 | 50%* Moss Base - 184017 F[2] |
| 150 | Nutmeg essential oil |
| 120 | Paradisone ®[3] |
| 250 | Sandela ®[4] |
| 400 | Sclareolate ®[5] |
| 700 | Vertofix Coeur ®[6] |
| 200 | Wolfwood ®[7] |
| 100 | Ylang oil |
| 3400 | |

*in dipropyleneglycol
[1] pentadecenolide; origin: Firmenich SA, Geneva, Switzerland
[2] compounded perfumery base; origin: Firmenich SA, Geneva, Switzerland
[3] methyl (1R)-cis-3-oxo-2-pentyl-1-cyclopentaneacetate; origin: Firmenich SA, Geneva, Switzerland
[4] 5-(2,2,3-trimethyl-3-cyclopentenyl)-3-methylpentan-2-ol; origin: Givaudan SA, Vernier, Switzerland
[5] propyl (S)-2-(1,1-dimethylpropoxy)propanoate; origin: Firmenich SA, Geneva, Switzerland
[6] methyl cedryl ketone; origin: International Flavors & Fragrances, USA
[7] (1S,2S,3S)-2,6,6-trimethyl-bicyclo[3.1.1]heptane-3-spiro-2'-cyclohexen-4'-one; origin: Firmenich SA, Geneva, Switzerland The addition of 400 parts by weight of Composition 1 (as described in Example 1) to the above-described composition imparted to the latter a diffusiveness and a "moist" effect, associated with the white flowers aspect of the composition, highly comparable to the effect provided when Lyral® was added instead of the invention's composition of matter.

Example 3

Preparation of a Perfuming Composition

A perfuming composition, of the floral, fruity, violet type, was prepared by admixing the following ingredients:

| Parts by weight | Ingredient |
|---|---|
| 60 | Benzyl acetate |
| 30 | Cinnamyl acetate |
| 30 | Citronellyl acetate |
| 30 | Geranyl acetate |
| 80 | 1%* Para Cresol acetate |

-continued

| Parts by weight | Ingredient |
|---|---|
| 120 | Phenylethyl acetate |
| 20 | 10%* (Z)-3-hexen-1-yl acetate |
| 30 | Hexyl acetate |
| 20 | Cinnamic alcool |
| 100 | Hexylcinnamic aldehyde |
| 60 | Ambrettolide ®[1)] |
| 10 | Anethol |
| 50 | Benzyl benzoate |
| 10 | Methyl benzoate |
| 50 | 2-Methyl-4-phenyl-2-butanol |
| 100 | Citronellol |
| 20 | Coumarine |
| 30 | 3-(4-Isopropylphenyl)-2-methylpropanal |
| 40 | 10%* Estragole |
| 40 | Eugenol |
| 200 | Exaltolide ®[2)] Total |
| 200 | Florol ®[3)] |
| 30 | 10%* Phenylethyl formiate |
| 2000 | 70%** Galaxolide ®[4)] |
| 50 | Geraniol |
| 800 | Habanolide ®[5)] |
| 1500 | Hedione ®[6)] HC |
| 200 | Helvetolide ®[7)] |
| 50 | 10%* Hivernal ®[8)] |
| 40 | Iralia ®[9)] |
| 30 | Methyl jasmonate |
| 600 | Lilial ®[10)] |
| 500 | Linalol |
| 40 | Methylisoeugenol |
| 30 | 10%* Methylnaphthylcetone |
| 20 | 10%* Methylparacresol |
| 200 | Muscenone ®[11)] Delta |
| 50 | Muscone Laevo |
| 20 | Nirvanol |
| 10 | 10%* Gamma nonalactone |
| 20 | 10%* (Z)-3-Hexen-1-ol |
| 60 | 10%* Benzyl propionate |
| 50 | Rose essential oil |
| 160 | Benzyl salicylate |
| 50 | Sclareolate ®[12)] |
| 500 | Tonalide ®[13)] |
| 20 | 10%* 2,4-Dimethyl-3-cyclohexene-1-carbaldehyde |
| 40 | Vanilline |
| 100 | Vertofix ®[14)] Coeur |
| 8500 | |

*in dipropyleneglycol
**in isopropyle myristate
[1)]16-hexadecanolide; origin: Firmenich SA, Geneva, Switzerland
[2)]pentadecanolide; origin: Firmenich SA, Geneva, Switzerland
[3)]tetrahydro-2-isobutyl-4-methyl-4(2H)-pyranol; origin: Firmenich SA, Geneva, Switzerland
[4)]1,3,4,6,7,8-hexahydro-4,6,6,7,8,8-hexamethyl-cyclopenta-g-2-benzopyrane; origin: International Flavors & Fragrances, USA
[5)]pentadecenolide; origin: Firmenich SA, Geneva, Switzerland
[6)]cis methyl dihydrojasmonate; origin: Firmenich SA, Geneva, Switzerland
[7)](1S,1'R)-2-[1-(3',3'-dimethyl-1'-cyclohexyl)ethoxy]-2-methylpropyl propanoate; origin: Firmenich SA, Geneva, Switzerland
[8)]3-(3,3/1,1-dimethyl-5-indanyl)propanal; origin: Firmenich SA, Geneva, Switzerland
[9)]mixture of methylionones isomers; origin: Firmenich SA, Geneva, Switzerland
[10)]3-(4-tert-butylphenyl)-2-methylpropanal; origin: Givaudan SA, Vernier, Switzerland
[11)]3-methyl-(5)-cyclopentadecenone; origin: Firmenich SA, Geneva, Switzerland
[12)]propyl (S)-2-(1,1-dimethylpropoxy)propanoate; origin: Firmenich SA, Geneva, Switzerland
[13)]3,3-dimethyl-5-(2,2,3-trimethyl-3-cyclopenten-1-yl)-4-penten-2-ol; origin: Firmenich SA, Geneva, Switzerland
[14)]methyl cedryl ketone; origin: International Flavors & Fragrances, USA The addition of 1500 parts by weight Composition 1 (as described in Example 1) to the above-described composition imparted to the latter a floral, lily of the valley connotation having an outstanding tenacity and an exceptional powdery sweetness.

The addition of Lyral® to the above perfuming composition, instead of the invention's composition, provided the same effect despite the several physic-chemical differences between the two compounds.

What is claimed is:

1. A compound of formula (IV') or (IV")

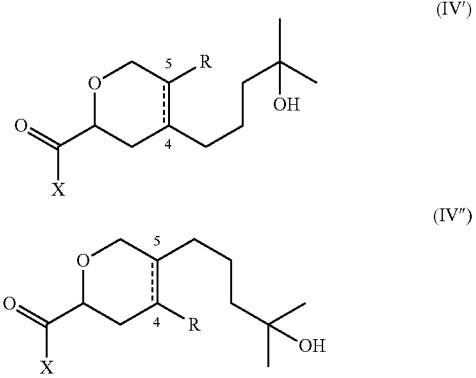

wherein X represent a hydrogen atom or a $OR^1$ group, $R^1$ being a $C_{1-4}$ alkyl group; and R represents
a hydrogen atom and the dotted line represents a carbon-carbon single or double bond; or
a $CH_2$ group bonded with C4 and C5 and the dotted line represents a carbon-carbon single bond; and
said compound (IV') or (IV") being in the form of any one of its stereoisomers or a mixture thereof.

2. A perfuming composition comprising
a composition of matter, comprising:
1) at least 70% of at least a compound of formula

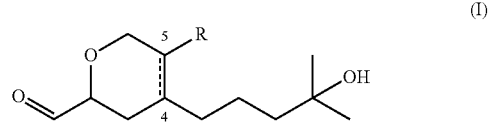

in the form of any one of its stereoisomers or a mixture thereof, and wherein R represents
a hydrogen atom and the dotted line represents a carbon-carbon single or double bond; or
a $CH_2$ group bonded with C4 and C5 and the dotted line represents a carbon-carbon single bond;
2) at most 30% of a compound of formula

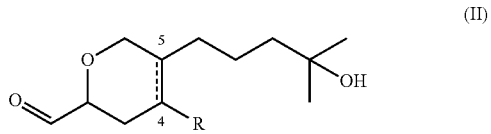

in the form of any one of its stereoisomers or a mixture thereof, and wherein R represents
a hydrogen atom and the dotted line represents a carbon-carbon single or double bond; or
a $CH_2$ group bonded with C4 and C5 and the dotted line represents a carbon-carbon single bond; and
wherein the percentages are w/w percentages relative to the total weight of the composition;
ii) at least one ingredient selected from the group consisting of a perfumery carrier and a perfumery base; and
iii) optionally at least one perfumery adjuvant.

3. The composition as recited in claim 2 comprising a perfuming consumer product characterized in that the perfumery consumer product is a perfume, a fabric care product, a body-care product, an air care product or a home care product.

4. A perfuming consumer product according to claim 3, characterized in that the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

5. The perfuming composition of claim 2, wherein the dotted line and R have simultaneously the same meaning in formula (I) and (II).

6. The composition as recited in claim 5, comprising a perfuming consumer product characterized in that the perfumery consumer product is a perfume, a fabric care product, a body-care product, an air care product or a home care product.

7. The composition as recited in claim 6, wherein the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

8. The perfuming composition of claim 2, wherein R represents a hydrogen atom and the dotted line represents a carbon-carbon single or double bond.

9. The composition as recited in claim 8, comprising a perfuming consumer product characterized in that the perfumery consumer product is a perfume, a fabric care product, a body-care product, an air care product or a home care product.

10. The composition as recited in claim 9, wherein the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

11. The perfuming composition of claim 2, wherein the compounds of formula (I) represent at least 85%, and the compounds of formula (II) at most 15%, of the total weight of the composition.

12. The composition as recited in claim 11, comprising a perfuming consumer product characterized in that the perfumery consumer product is a perfume, a fabric care product, a body-care product, an air care product or a home care product.

13. The composition as recited in claim 12, wherein the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

14. The perfuming composition of claim 2, wherein the composition comprises 88% of 4-(4-hydroxy-4-methylpentyl)-3,6-dihydro-2H-pyran-2-carbaldehyde and 12% of 5-(4-hydroxy-4-methylpentyl)-3,6-dihydro-2H-pyran-2-carbaldehyde.

15. The composition as recited in claim 14, comprising a perfuming consumer product characterized in that the perfumery consumer product is a perfume, a fabric care product, a body-care product, an air care product or a home care product.

16. A perfuming consumer product according to claim 15, characterized in that the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

17. A method to confer, enhance, improve or modify the odor properties of a perfuming composition or of a perfumed article, which method comprises adding to said composition or article an effective amount of a perfuming ingredient of a composition of matter comprising:

1) at least 70% of a compound of formula

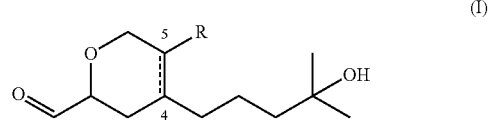

(I)

in the form of any one of its stereoisomers or a mixture thereof, and wherein R represents
a hydrogen atom and the dotted line represents a carbon-carbon single or double bond; or
a $CH_2$ group bonded with C4 and C5 and the dotted line represents a carbon-carbon single bond;

2) at most 30% of a compound of formula

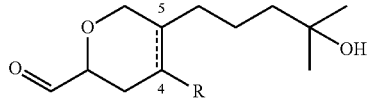

(II)

in the form of any one of its stereoisomers or a mixture thereof, and wherein R represents
a hydrogen atom and the dotted line represents a carbon-carbon single or double bond; or
a $CH_2$ group bonded with C4 and C5 and the dotted line represents a carbon-carbon single bond; and
wherein the percentages are w/w percentages relative to the total weight of the composition.

18. The method according to claim 17, wherein the dotted line and R have simultaneously the same meaning in formula (I) and (II).

19. The method according to claim 17, wherein R represents a hydrogen atom and the dotted line represents a carbon-carbon single or double bond.

20. The method according to claim 17, wherein the compounds of formula (I) represent at least 85%, and the compounds of formula (II) at most 15%, of the total weight of the composition.

21. The method according to claim 17, wherein the composition comprises 88% of 4-(4-hydroxy-4-methylpentyl)-3,6-dihydro-2H-pyran-2-carbaldehyde and 12% of 5-(4-hydroxy-4-methylpentyl)-3,6-dihydro-2H-pyran-2-carbaldehyde.

* * * * *